United States Patent
Miura (12)

(10) Patent No.: US 6,395,521 B1
(45) Date of Patent: May 28, 2002

(54) MICROBIAL PROCESS FOR PRODUCING HYDROGEN

(76) Inventor: Yoshiharu Miura, 21-12, Koyoenmegamiyama-cho, Nishinomiya-shi (JP), 662-0011

( * ) Notice: Subject to any disclaimer, the term of this patent is extended or adjusted under 35 U.S.C. 154(b) by 0 days.

(21) Appl. No.: 09/786,771

(22) PCT Filed: Feb. 14, 2000

(86) PCT No.: PCT/JP00/00807

§ 371 (c)(1),
(2), (4) Date: Apr. 25, 2001

(87) PCT Pub. No.: WO01/02595

PCT Pub. Date: Jan. 11, 2001

(30) Foreign Application Priority Data

Jul. 6, 1999 (JP) ............................................ 11-191166

(51) Int. Cl.$^7$ .............................. C12P 3/00; C12P 7/56; C12P 7/06; C12P 7/24
(52) U.S. Cl. ..................... 435/168; 435/161; 435/162; 435/139
(58) Field of Search ................................. 435/168, 161, 435/162, 139

(56) References Cited

U.S. PATENT DOCUMENTS 5,578,472 A * 11/1996 Ueda et al. .................. 435/161

FOREIGN PATENT DOCUMENTS

| EP | PCT/US96/11146 | 7/1996 |
| JP | 58(1983)-60992 | 4/1983 |
| JP | 8(1996)-280393 | 10/1996 |
| JP | 10(1996)-42881 | 2/1998 |
| JP | 2000-102397 | 4/2000 |

OTHER PUBLICATIONS

Akano et al. Hydrogen Production by Photosynthetic microorganisms. 1996.Applied Biochemistry and Biotechnology, 57/58: 677–688.*

P. Hillmer et al.;$H_2$ Metabolism in the Photosynthetic Bacterium Rhodopseudomonas capsulata: $H_2$ Production by Growing Cultures; Feb. 1977; Journal of Bacteriology; American Society for Microbiology; pp. 724–731.

P. Hillmer et al.; $H_2$ Metabolism in the Photosynthetic Bacterium Rhodopseudomonas capsulata: Production and Utilization of $H_2$ by Resting Cells; Feb. 1977; Journal of Bacteriology; American Society of Microbiology; pp. 732–739.

Miura, "Hydrogen production based on photosynthesis by a microalga", *Farumashia*, vol. 26, pp. 419–422 (1990).

Miura et al., "Stably Sustained Hydrogen Production with High Molar Yield through a Combination of a Marine Green Alga and a Photosynthetic Bacterium", *Biosci. Biotech. Biochem.*, vol. 56(5), pp. 751–754 (1992).

Merchuk et al., "Improving the Airlift Reactor: The Helical Flow Promoter", 3$^{rd}$ International Conference on Bioreactor and Bioprocess Fluid Dynamics, BHR Group Conference Series, Publication No. 5, 8 pp. (1993).

Miura et al., "Stably Sustained Hydrogen Production By Biophotolysis in Natural Day/Night Cycle", *Energy Convers. Mgmt.*, vol. 38, Suppl., pp. S533–S537 (1997).

* cited by examiner

*Primary Examiner*—Jon P. Weber
*Assistant Examiner*—Kailash C. Srivastava
(74) *Attorney, Agent, or Firm*—Webb Ziesenheim Logsdon Orkin & Hanson, P.C.

(57) ABSTRACT

In hydrogen production with microorganisms, cultivation of a microalga under light and aerobic conditions and/or hydrogen production by a photosynthetic bacterium under light and anaerobic conditions are performed with a transparent tower-type air-lift culture tank. Hydrogen can be produced more efficiently with a dual cylindrical structure and a helical flow promoter.

3 Claims, 1 Drawing Sheet

MICROBIAL PROCESS FOR PRODUCING HYDROGEN

TECHNICAL FIELD

The present invention relates to a method for producing hydrogen by microorganisms. More specifically, the present invention relates to a method for producing hydrogen efficiently with a microalga having a photosynthetic ability and a bacterium having a photosynthetic ability, utilizing solar energy.

BACKGROUND ART

In recent years, global warming has been a main factor that causes abnormal weather worldwide and breaks the global ecosystem, so that prevention of global warming is a worldwide issue that should be addressed urgently. It has turned out that global warming is caused mainly by a large consumption of fossil fuel including oil and coal and the resulting warming gases such as carbon dioxide ($CO_2$). In this context, there is a strong demand for research in new technologies for suppressing the release of global warming gases, creation of energy sources, such as hydrogen, utilizing biofunctions, and study of immobilization and degradation of global warming gases.

Among these, hydrogen energy is advantageous in that it can be converted to electrical energy with high efficiency in the form of a fuel cell, the amount of the generated heat is 3 or 4 times that generated by oil, only water is generated after combustion so that there is no fear of environmental pollution, and that water, which is the raw material for hydrogen energy, is abundant.

Various studies for production of hydrogen energy utilizing biofunctions have been conducted. For example, Japanese Laid-Open Patent Publication (Tokkai) No. 58-60992 discloses a method for producing hydrogen by culturing a green alga having a photosynthetic ability and a hydrogen producing ability under light and aerobic conditions and degrading the photosynthesized and accumulated substances under dark and slightly aerobic conditions to produce hydrogen. Furthermore, Farmacia vol. 26, 419–422 (1990) reports that among green algae, the Chlamydomonas sp. strain MGA161 has a high hydrogen producing ability. Biosci. Biotech. Biochem., vol. 56, 751–754 (1992) reports that hydrogen can be produced efficiently by degrading the photosynthetic products by Chlamydomonas sp. strain MGA161 under dark and anaerobic conditions and allowing a bacterium having a photosynthetic ability (hereinafter, referred to as "photosynthetic bacterium") to act on the degraded products. This article describes that the photosynthetic bacterium produces hydrogen, using ethanol, acetic acid, formic acid, lactic acid, etc., which are products of fermentative degradation of the photosynthetic products by the green alga, as electron donors. On the other hand, the article also reports that hydrogen production cannot be achieved simply with ethanol or acetic acid. Thus, the mechanism for the production of hydrogen is not clear, and therefore optimum conditions have not been established yet.

On the other hand, hydrogen production with a bacterium is not performed on an industrial scale, because of its culture apparatus. For example, cultivation of a photosynthetic green alga and a photosynthetic bacterium requires light, but light cannot reach the deep portion of a culture tank. Therefore, the culture tank should be shallow, which causes a problem with regard to the culture site that a large floor area is required for mass cultivation. In addition, a shallow culture causes a problem with regard to the culture conditions as follows. Since the culture tank is shallow, dissolution of carbon dioxide in the culture medium is insufficient, so that the cultivation is inefficient. Moreover, continuous cultivation is also difficult.

In order to solve these problems, methods for culturing with stirring while irradiating the culture with artificial light have been examined. However, there are some problems with regard to insufficiency of light that can reach the inside, irradiation time of cells with light, and irradiation quantity. Furthermore, the cost of artificial light is problematic, so that problems for mass production of hydrogen remain unsolved.

Therefore, in systems for hydrogen production with a microalga and a photosynthetic bacterium, there is a need to establish efficient cultivation of a photosynthetic microalga and optimum conditions for hydrogen production by a photosynthetic bacterium that uses products by fermentative degradation of photosynthetic products as substrates.

BACKGROUND OF THE INVENTION

It is an object of the present invention to solve the above problems, and provide efficient cultivation of a photosynthetic microalga and optimum conditions for hydrogen production by a photosynthetic bacterium that uses products by fermentative degradation of photosynthetic products as substrates, as well as a method for mass production of hydrogen by microorganisms.

The present invention provides a method for producing hydrogen comprising preparing photosynthetic products by culturing a microalga having a photosynthetic ability under light and aerobic conditions; preparing a fermentation solution of the photosynthetic products by culturing the microalga under dark and anaerobic conditions; and allowing a bacterium having a photosynthetic ability to act on the fermentation solution under light and anaerobic conditions, wherein the process of culturing the microalga under light and aerobic conditions and/or the process of allowing the bacterium having a photosynthetic ability to act on the fermentation solution under light and anaerobic conditions are performed with a transparent tower-type air-lift culture tank.

In a preferable embodiment, the tower-type air-lift culture tank is of a dual cylindrical structure.

In another preferable embodiment, the tower-type air-lift culture tank is of a structure in which a helical flow is generated.

In still another preferable embodiment, the subsequent processes are performed continuously: preparing photosynthetic products by culturing the microalga having a photosynthetic ability under light and aerobic conditions; preparing a fermentation solution of the photosynthetic products by culturing the microalga under dark and anaerobic conditions; and allowing a bacterium having a photosynthetic ability to act on the fermentation solution for hydrogen production under light and anaerobic conditions.

In yet another preferable embodiment, in the process of allowing the bacterium having a photosynthetic ability to act on the fermentation solution under light and anaerobic conditions, a lactic acid content is regulated to at least 0.3 mM.

According to another aspect of the present invention, a method for producing hydrogen includes preparing photosynthetic products by culturing a microalga having a photosynthetic ability under light and aerobic conditions; preparing a fermentation solution of the photosynthetic products by culturing the microalga under dark and anaerobic conditions; and allowing a bacterium having a photosynthetic ability to act on the fermentation solution under light and anaerobic conditions, wherein a lactic acid content in the fermentation solution under the dark and anaerobic conditions is regulated to at least 0.3 mM.

DETAILED DESCRIPTION OF THE INVENTION

Figure 1:
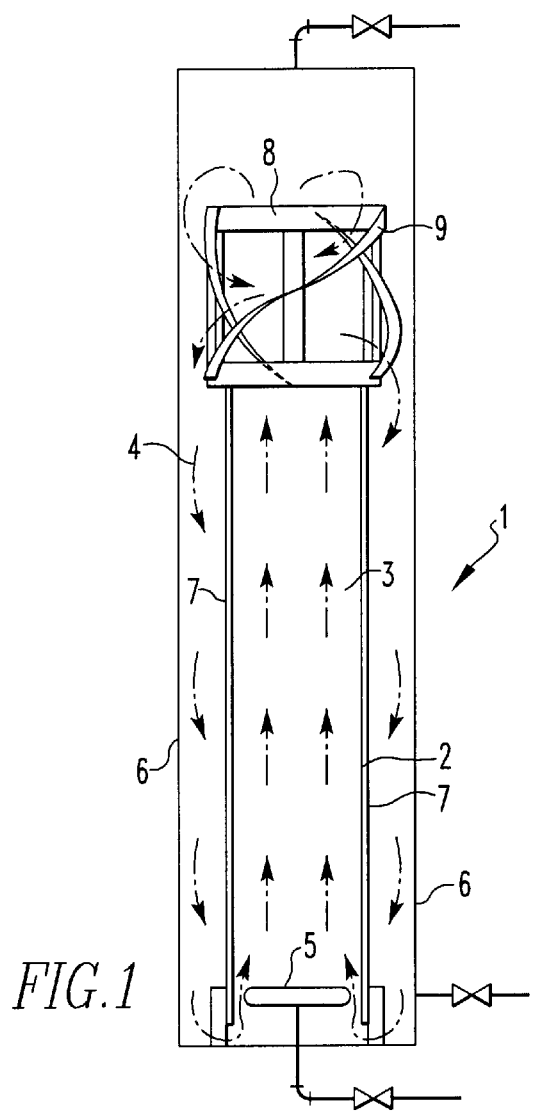
FIG. 1 is a schematic view of a culture tank used in the present invention.

There is no limitation regarding microalgae used in the present invention, as long as they have a photosynthetic ability. In particular, green algae and blue-green algae are used preferably. Examples of green algae include *Chlamydomonas reinhardtii, Chlamydomonas moewusii,* Chlamydomonas sp. strain MGA161, *Chlamydomonas eugametos*, and *Chlamydomonas segnis* belonging to Chlamydomonas; *Chlorella vulgaris* belonging to Chlorella; *Senedesmus obliguus* belonging to Senedesmus; and *Dunaliella tertrolecta* belonging to Dunaliella. Examples of blue-green algae include *Anabaena variabilis* ATCC 29413 belonging to Anabaena, Cyanothece sp. ATCC 51142 belonging to Cyanothece, Synechococcus sp. PCC 7942 belonging to Synechococcus and *Anacystis nidulans* belonging to Anacystis.

Among these, green alga Chlamydomonas sp. strain MGA161, which is isolated from seawater by a conventional method, is preferable because of the following excellent abilities. The photosynthetic ability of strain MGA161 is high under light and aerobic conditions, and its fermentation rate is fast under dark and anaerobic conditions. Furthermore, when returned to light and aerobic conditions, strain MGA161 can adapt quickly to the photosynthetic system. Therefore, this strain is preferred. Chlamydomonas sp. strain MGA161 or other strains corresponding thereto easily can be isolated from seawater samples based on a photosynthetic ability and a degradation ability by those skilled in the art.

The cultivation of a microalga under light and aerobic conditions can be performed in a medium containing inorganic components under irradiation with solar light and/or artificial light, using a transparent tower-type air-lift culture tank. The cultivation temperature is about 15° C. to about 40° C., preferably about 25° C. to about 35° C.

As a medium for culturing a microalga, especially, a green alga, any medium can be used, as long as it contains a suitable nitrogen supply source and inorganic components. As a medium containing inorganic components, seawater can be used preferably, but a modified Okamoto medium (hereinafter, referred to as MOM medium) having the following composition also can be used:

| | |
|---|---|
| NaCl | 30 g |
| $CaCl_2.2H_2O$ | 200 mg |
| $MgSO_4.7H_2O$ | 250 mg |
| $FeSO_4.7H_2O$ | 20 mg |
| $KH_2PO_4$ | 40.8 mg |
| $K_2HPO_4$ | 495 mg |

-continued

| | | |
|---|---|---|
| Vitamin $B_1$ | 100 μg | |
| Vitamin $B_{12}$ | 1 μg | |
| 1M $NH_4Cl$ | 5 ml | |
| a trace amount of metal mixture A5 | 1.0 ml | |
| distilled water | 1000 ml | pH 8.0 |

Herein, the composition of the trace amount of metal mixture A5 is as follows:

| | |
|---|---|
| $H_3BO_4$ | 2.85 g |
| $MnCl_2.4H_2O$ | 1.81 g |
| $ZnSO_4.7H_2O$ | 0.22 g |
| $CuSO_4.5H_2O$ | 0.08 g |
| $Na_2MoO_4$ | 0.021 g |
| $CaCl_2.6H_2O$ | 0.01 g |
| EDTA.2Na | 50 g |
| distilled water | 1000 ml |

Hydrogen production under light and anaerobic conditions by a photosynthetic bacterium generally depends on nitrogenase. The nitrogenase activity is inhibited depending on the concentration of a nitrogen source (e.g., ammonium chloride, glutamate). In the present invention, a light and aerobic culture solution with a concentrated microalga can be used for fermentative degradation of photosynthetic products under dark and anaerobic conditions, and the resultants can be used for hydrogen production by a photosynthetic bacterium under light and anaerobic conditions. Therefore, a lower concentration of nitrogen source in the medium of microalga cultivation under light and aerobic conditions is preferable. In the case of ammonium chloride, the concentration is adjusted to 5 mM or less, preferably 2.5 mM or less, more preferably 0.5 mM or less. In the case of other nitrogen sources, it is preferable to make the concentration as low as possible not to inhibit nitrogenase.

Therefore, in the cultivation of a microalga, especially, a green alga, it is preferable to modify the MOM medium ($NH_4Cl$ concentration: 5 mM) so that the concentration of ammonium chloride is as low as possible, preferably 0.5 mM or less. When cultivation is performed in 0.5 mM or less of ammonium chloride, the concentration of accumulated starch can be higher than in the case of 5 mM.

In the present invention, carbon dioxide is required as a carbon source to culture a microalga, and therefore the microalga is aerated with air or a mixed gas of air and carbon dioxide. If carbon dioxide is mixed, it is preferable to mix carbon dioxide in a ratio of about 2% to about 10%, preferably about 2% to about 5%.

In the present invention, solar light is utilized with a transparent tower-type air-lift culture tank. Therefore, irradiation with light is not necessary, but light-irradiation equipment can be provided in view of shortage of sunshine on cloudy or rainy days. Light-irradiation equipment is required for continuous cultivation at night.

The transparent tower-type air-lift culture tank can be made of any material, as long as it is transparent and transmits solar light and/or artificial light. Examples thereof include transparent plastics such as (reinforced) acrylic resin, polycarbonate, polypropylene, polyterephthalate, and glass.

Furthermore, a heating and/or cooling apparatus can be provided in an upper portion and/or a lower portion of the culture tank to regulate the temperature of the culture solution.

The air-lift culture tank can be in any form, as long as it has an aeration apparatus such as a nozzle, a ring-shaped sparger, or a porous plate to circulate liquid. The cells (microalgae) in the vicinity of the wall of the culture tank most intensely receive light (solar light or artificial light) with which the air-lift culture tank is irradiated, but as the cell amount is increased, the light hardly reaches the inside so that photosynthesis (growth) becomes insufficient. Furthermore, too much light adversely affects growth of cells. Therefore, appropriate fluidity of cells and appropriate miscibility of the cells on the inner side of the tank and the cells on the outer side (on the surface side) of the tank are required.

In the present invention, it is preferable that the inside of the transparent tower-type air-lift culture tank is of a dual cylindrical structure. Hereinafter, the culture tank will be described with reference to FIG. 1. The culture tank 1 of the present invention is preferably cylindrical. An inner cylinder 2 (which may be referred to simply as "cylinder") is supported in a lower portion of the culture tank 1, separated from the bottom by a space through which liquid can flow. Thus, a culture solution 3 inside the cylinder 2 and a culture solution 4 outside the cylinder 2 are circulated. Air is allowed to flow from the lower portion of the cylinder 2 provided in the culture tank by an aeration apparatus 5 (e.g., ring shaped sparger) so that a flow of a culture solution from the lower portion to the upper portion of the inside of the cylinder 2 is formed. Then, the culture solution is circulated from the upper surface of the inside of the cylinder 2 to the outside of the cylinder 2. The culture solution flows along the space between the tank wall 6 and the cylinder 2 to the lower portion of the culture tank. Thus, the culture solution is circulated. When flowing between the tank wall 6 and the outer wall 7 of the cylinder, the culture solution receives light (solar light) most intensely and photosynthesis proceeds. Thus, by providing the dual cylindrical structure inside the transparent tower-type air-lift culture tank 1, the microalga culture solution flows between the tank wall 6 and the outer wall 7 of the cylinder, so that the irradiation time of the microalga with light can be prolonged and the microalga can be circulated efficiently. Consequently, photosynthesis (growth) of the microalga can be effected more efficiently than when a conventional stirring type culture tank is used.

In the present invention, it is preferable that the cylinder used in the present invention is also transparent. The material thereof can be the same as that of the transparent culture tank, or it can be a different material.

In the present invention, it is preferable that a structure that causes a helical flow is provided in the tower-type air-lift culture tank. The helical flow is described in the article of Merchuk et al. (the 3rd INTERNATIONAL CONFERENCE on Bioreactor and Bioprocess Fluid Dynamics, pp. 61 to 68). In general, in conventional circulation type air-lift culture tanks, a flow in the tank moves only in the vertical direction, and cells close to the outer surface receive intense light. Thus, growth is inhibited. On the other hand, inner cells lack necessary light for photosynthesis. Therefore, a radial flow is generated so that light energy necessary for photosynthesis is supplied uniformly to all the cells. To meet this purpose, for example, an apparatus that generates a helical flow, helical flow promoter 8, can be used. As shown in FIG. 1, this apparatus 8 is provided in such a manner that a helical or radial flow is generated when several fins or baffles 9 are provided in the water. The apparatus 8 is provided in an upper portion of the inner cylinder 2 of the air-lift culture tank 1 to allow the culture solution to flow radially or helically toward the downstream. With this apparatus provided in an upper portion of the inner cylinder 2, the culture solution is also stirred as it flows between the tank wall 6 and the outer wall 7 of the cylinder. Therefore, the culture solution can be irradiated with light uniformly and for a long time without excessive exposure of the microalgae to light (solar light). Thus, photosynthesis proceeds more efficiently than in a structure provided simply with dual cylinders.

The size of the air-lift culture tank and the size of the inner cylinder of the present invention can be selected as appropriate in view of the materials and the culture scale.

In the present invention, the aeration quantity can be selected in view of the culture rate. In general, when a helical flow apparatus is used, cells can flow in a smaller aeration quantity than when no helical flow apparatus is provided. Too much aeration quantity is not preferable because the helical flow apparatus causes an air pocket.

In the culture process of the microalgae, it is desirable to collect as many of the microalga in the logarithmic growth phase as possible, because the subsequent fermentation (degradation of photosynthetic products) under dark and anaerobic conditions can be performed smoothly. Furthermore, when culturing the microalga, it is preferable to perform a continuous cultivation because then the microalga can have a high growth rate and the logarithmic growth phase can be maintained.

The obtained microalga is transferred to a fermentation tank, where a process of fermentation of photosynthetic products is performed under dark and anaerobic conditions. In this process, photosynthetic products, such as starch, are degraded and fermented so that organic acids such as formic acid, acetic acid, and lactic acid and alcohols such as ethanol and glycerol are released from the microalga cells. These organic compounds are used as electron donors for hydrogen production by photosynthetic bacteria. Therefore, dark and anaerobic conditions are preferable that generally can achieve smooth production of the organic compounds by fermentation. In particular, conditions where a large amount of lactic acid can be produced by fermentation are most preferable.

There is no limitation regarding the fermentation tank used for fermentation under dark and anaerobic conditions. It is preferable that the gas phase space in the upper portion of the fermentation tank is as small as possible. In order to maintain the anaerobic conditions, it is preferable to introduce carbon dioxide or a mixed gas of carbon dioxide and an inert gas to the upper space to create an atmosphere with no oxygen or little oxygen so that degradation of photosynthetic products is promoted and hydrogen production by microalgae is suppressed as much as possible. Bubbling of inert gas is not preferable. Stirring can be very mild.

A higher microalga concentration is more preferable when fermentation of a microalga under dark and anaerobic conditions is performed, because the concentrations of organic acid or alcohol in a degradation solution that is used as a substrate of a photosynthetic bacterium under the subsequent light and anaerobic conditions can be high. Therefore, it is preferable to concentrate the microalga culture solution, for example, by concentration or separation techniques such as membrane separation and centrifugation. Furthermore, for continuous cultivation under light and aerobic conditions, the microalga is transferred to a fermentation tank under dark and anaerobic conditions while being concentrated continuously.

A preferable fermentation temperature of the microalga under dark and anaerobic conditions is about 10° C. to about 40° C., preferably about 25° C. to about 35° C.

It is preferable that in fermentation of the microalga under dark and anaerobic conditions, lactic acid is secreted in the degradation solution. In the present invention, it has been shown that lactic acid induces production of nitrogenase. More specifically, hydrogen cannot be produced without the presence of lactic acid. It is preferable that the lactic acid concentration is at least 0.3 mM.

Furthermore, in the process of preparing a fermentation solution under dark and anaerobic conditions, it is preferable to perform continuous fermentation in a relatively small dilution ratio, namely, with a long residence time, because then a fermentation solution having a high level of degradation of photosynthetic products can be obtained continuously, and the fermentation solution can be supplied continuously to the subsequent hydrogen production process with photosynthetic bacteria under light and anaerobic conditions.

The degradation solution (fermentation solution) obtained by fermenting the microalga under dark and anaerobic conditions is separated from the microalga, and used as a substrate for the subsequent process of hydrogen production by a photosynthetic bacterium under light and anaerobic conditions. All or part of the microalga is used again for photosynthesis under light and aerobic conditions.

As a transparent tower-type air-lift culture tank used in the process for allowing a photosynthetic bacterium to act on under light and anaerobic conditions, the same as used for cultivation of the microalga under light and aerobic conditions can be used.

The anaerobic conditions can be created by allowing inert gas such as argon, hydrogen, or a mixed gas of carbon dioxide and hydrogen to flow. Hydrogen or a mixed gas of carbon dioxide and hydrogen at a ratio of 1:1 is preferable, in view of the collection of generated gas. It is preferable to circulate hydrogen while drawing out part of the hydrogen. The cultivation temperature of a photosynthetic bacterium is about 10° C. to about 40°C., preferably about 25° C. to about 35° C.

As a photosynthetic bacterium, a photosynthetic lithotrophic bacterium and a photosynthetic organotrophic bacterium (purple nonsulfur bacterium, green gliding bacterium, etc.) can be used. In the present invention, organic compounds generated by degradation of photosynthetic products are used as a substrate (an electron donor), and therefore a photosynthetic organotrophic bacterium can be used preferably. Examples of photosynthetic organic vegetative bacteria include purple nonsulfur bacteria belonging to Rhodospirillaceae and green gliding bacteria belonging to Chloflexaceae.

As such a photosynthetic organotrophic bacterium, for example, a microorganism that produces hydrogen from seawater, using lactic acid (for example, 0.3 mM) as a substrate can be selected. Examples of photosynthetic bacteria include *Rhodopseudomonas palustris* and *Rhodopseudomonas acidophila* belonging to Rhodopseudomonas, and *Rhodospirillum rubrum* ATCC 11170, *Rhodospirillum rubrum* IFO 3986 belonging to Rhodospirillum, *Rhodobacter sphaeroides, Rhodobacter capsulatus* ATCC 23782, ATCC 17013 belonging to Rhodobacter, and *Rhodovulum strictum, Rhodovulum adriaticum*, and *Rhodovulum sulfidophilum* belonging to Rhodovulum.

In the present invention, the strain named *Rhodovulum sulfidophilum* isolated from a seawater sample (which may be referred to simply as W-1S) and photosynthetic bacteria having activity equal to that of this strain can be used preferably.

It is preferable that the photosynthetic bacterium under light and anaerobic conditions is immobilized on a carrier. This is preferable because of its recyclablity and no need of growth, and is advantageous for continuous treatment of a fermentation solution.

To immobilize the photosynthetic bacterium, for example, known methods such as carrier binding, crosslinking, and entrapment can be used, but carrier binding is most preferable. Carrier binding includes chemical adsorption, in which photosynthetic bacterium is adsorbed to an ion exchange resin, and physical adsorption. Examples of the material of the carrier used in the present invention include foams and resins such as porous glass beads, polyvinyl alcohol, polyurethane foam, polystyrene foam, polyacrylamide, polyvinyl formal resin porous material, silicon foam, and cellulose porous material. The pore size of the porous material is preferably about 10 $\mu$m to about 500 $\mu$m.

The shape of the carrier can be any shape, but a sphere or cube is preferable in view of the strength of the carrier and cultivation efficiency. A preferable size is 2 mm to 50 mm in diameter for a spherical carrier, and 2 mm to 50 mm×2 mm to 50 mm for a cubic carrier.

The microalga can also be immobilized. It is preferable to use the immobilized microalga for continuous photosynthesis under light and aerobic condition and continuous fermentation under dark anaerobic condition.

As described above, since nitrogenase involved in hydrogen production of a photosynthetic bacterium is inhibited by nitrogen, it is preferable that the nitrogen source concentration in the reaction solution under light and anaerobic conditions is as low as possible.

The fermentation solution under dark and anaerobic conditions contains organic acids (formic acid, acetic acid, lactic acid, etc.), alcohols (ethyl alcohol, glycerol, etc.), which are products resulting from degradation of photosynthetic products. The organic acids serve as electron donors for hydrogen production. The inventors of the present invention found that among these, as shown in Example 1, lactic acid is an inducer of nitrogenase involved in hydrogen production, and confirmed that nitrogenase is induced in proportion to the concentration of lactic acid until a given concentration (about 0.3 mM) of lactic acid is reached. Therefore, it is preferable to maintain the lactic acid concentration at 0.3 mM or more to promote hydrogen production. Therefore, the present invention encompasses embodiments where hydrogen is produced under light and anaerobic conditions while adding lactic acid.

Furthermore, organic acids other than lactic acid, for example, malic acid or succinic acid can induce nitrogenase, and therefore malic acid or succinic acid can be used in place of lactic acid, or can be used together with lactic acid.

Furthermore, continuous cultivation and hydrogen production can be achieved by culturing a microalga under light and aerobic conditions continuously (that is, irradiation with light is also performed at night), subjecting the obtained microalga cells sequentially to fermentation under dark and anaerobic conditions, and supplying the fermentation solution under dark and anaerobic conditions continuously to a photosynthetic bacterium under light and anaerobic conditions.

EXAMPLES

Hereinafter, the present invention will be described by way of examples employing a green alga as a microalga, but the present invention is not limited to these examples.

Example 1

Culturing a Green Alga in a Transparent Tower-type Air-lift Culture Tank

FIG. 1 shows a culture tank 1 used under light and aerobic conditions and light and anaerobic conditions used in the present invention. A cylinder 2 made of acrylic resin having an inner diameter of 17.5 cm and a height of 346 cm was provided in a portion elevated 4 cm above the bottom of the cylindrical culture tank 1, which is made of acrylic resin and has an inner diameter of 28 cm and a height of 380 cm (a volume of about 230 L). A culture solution in the culture tank 1 can circulate between the inside and the outside (the space provided by the culture tank wall 6 and the outer surface 7 of the cylinder) of the cylinder. Thus, the culture tank 1 is of a dual cylindrical structure. A ring-shaped sparger 5 having a diameter of 12 cm was provided in a portion 10 cm higher from the bottom. The sparger was a tube having *a diameter of 1 cm, and was provided with 50 holes of 1 mm. A helical flow promoter 8 was provided in an upper portion of the cylinder so that a helical flow was generated from the upper portion of the culture tank toward the lower portion in a space between the inner wall 6 of the culture tank and the outer wall 7 of the inner cylinder.

In the light and aerobic conditions, solar light and a light source (18 W/m$^2$) were used. A medium was prepared by further modifying the modified Okamoto medium and dissolving ammonium chloride in the modified medium at a concentration of 0.5 mM. A green alga Chlamydomonas sp. strain MGA161 was inoculated in 200 L of the medium in a ratio of 3.5 μg of dry weight/ml, and was aerated with 0.3 vvm of air containing 5% of carbon dioxide to initiate cultivation. Then, when the logarithmic growth phase was entered, continuous cultivation was initiated. The dilution ratio was 0.083/hr.

The growth rate of the green alga strain MGA161 in this cultivation was 0.267 g/L/hr. This value corresponded to twice the value when a culture solution of the same volume was cultured in a raceway type culture tank (actual volume of 200 L) of 35 cm depth, while irradiated with light with 18 W/m$^2$ and aerated with 0.3 vvm of air containing 5% of carbon dioxide. The floor area of the transparent air-lift type culture tank used in this experiment was about 1/10 of the raceway type culture tank. Therefore, the amount of the produced alga cells per unit floor area of the transparent air-lift type culture tank was about 20 times as much as that of the raceway type culture tank, which proved that the transparent air-lift type culture tank was advantageous.
Degradation of Photosynthetic Products and Hydrogen Production Under Light and Anaerobic Conditions While concentrating the green alga to about twice the original concentration by subjecting a culture solution extracted from the culture in continuous cultivation to a small continuous membrane separator, the culture solution was transferred to a fermentation tank under dark and anaerobic conditions. This fermentation tank was made of stainless steel, had a volume of 100 L and was provided with a stirring blade. Fermentation under dark and anaerobic conditions was performed at about 30° C. while circulating carbon dioxide in the gas phase and stirring very mildly.

The fermentation under dark and anaerobic conditions was performed for 12 hours, and after completion of the fermentation, the green alga was separated from the fermentation solution. Then, part of the green alga was returned to the culture under light and aerobic conditions for photosynthesis. On the other hand, the lactic acid concentration of the fermentation solution was 0.32 mM. The lactic acid concentration was obtained by separation with HPLC (high-performance liquid chromatogram) and quantitative analysis at an absorbance of 210 nm.

The photosynthetic bacterium used under the light and anaerobic conditions was W-1S, and was previously obtained by aerobically culturing with the modified Okamoto medium containing 1.0 g/l of sodium succinate, 1.0 g/l of sodium acetate, 1.0 g/l of sodium malate, 1.0 g/l of sodium pyruvate, and 1 mM of ammonium chloride at 30° C. for 24 hours. The photosynthetic bacterium (W-1S) was added so that the amount of dry weight was 2 g per 1 L of the fermentation solution. The cultivation under the light and anaerobic conditions was performed at 30° C. while circulating a mixed gas of carbon dioxide and hydrogen of 1:2 at 1 vvm for aeration. The produced hydrogen was separated from carbon dioxide by passing through an alkaline solution and collected.

The culture tank used was the same type as that used for culturing a green alga in Example 1, and the amount of the added fermentation solution and the position of the helical flow promoter were also the same.

As a result of a reaction for 12 hours, hydrogen was produced in an amount of 585 ml/g of dry weight of cells. This amount of the produced hydrogen corresponded to about 2.6 times the amount when hydrogen was produced with a parallel plate type photobioreactor having a height of 50 cm and the same volume under the same conditions. The floor area of the transparent air-lift type culture tank was about 1/7.5 of the parallel plate type photobioreactor. Therefore, the amount of the produced hydrogen per unit floor area of the transparent air-lift type culture tank was about 19 times as much as that of the parallel plate type photobioreactor, which proved that the transparent air-lift type culture tank was advantageous.

Example 2

Figure 2:
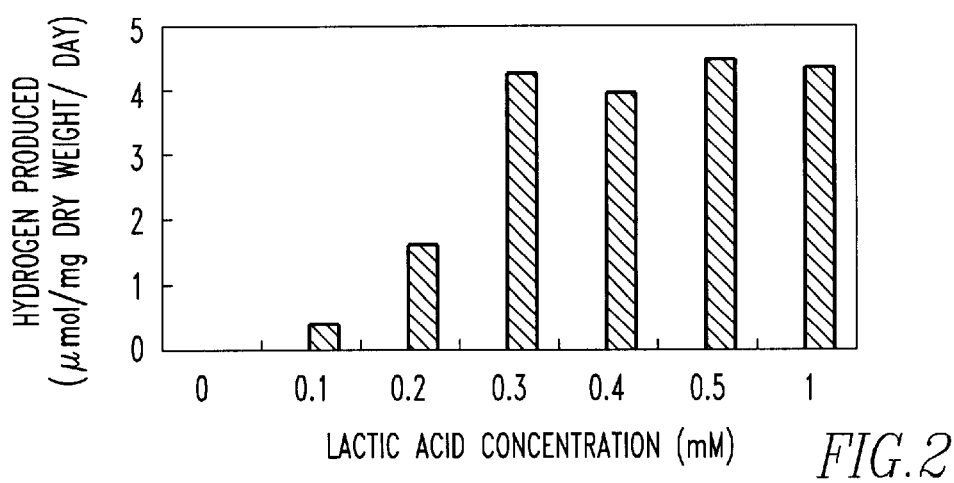
FIG. 2 is a graph showing that lactic acid is essential to hydrogen production and that the optimum concentration of lactic acid is 0.3 mM or more.

The effects of organic acids on hydrogen production by a photosynthetic bacterium under light and anaerobic conditions were examined. Lactic acids in amounts of 0, 0.1, 0.2, 0.3, 0.4, 0.5 and 1 mM were added to modified Okamoto media containing 0.6 mM of acetic acid, 1.5 mM of ethanol and 0.5 mM of glycerol, and the amounts of hydrogen produced by W-1S were measured. FIG. 2 shows the results. In FIG. 2, no hydrogen was produced in a medium without lactic acid, whereas hydrogen was produced in a medium containing lactic acid. The results indicate that lactic acid induces production of nitrogenase. Hydrogen production increased in a lactic acid concentration-dependent manner until the concentration reached 0.3 mM. However, it did not increase when the concentration was more than that. Therefore, it was found that when lactic acid is contained in a concentration of at least 0.3 mM, hydrogen is produced in a substantially constant amount.

Although it is not shown in the data, it was also demonstrated that malic acid and succinic acid also induce production of nitrogenase.

In hydrogen production with a microalga, cultivation of the microalga under light and aerobic conditions and/or hydrogen production by a photosynthetic bacterium under light and anaerobic conditions can be performed efficiently by using a transparent tower-type air-lift culture tank.

What is claimed is:

1. A method for preparing hydrogen comprising:
preparing photosynthetic products by culturing a microalga having a photosynthetic ability under light and aerobic conditions;
preparing a fermentation solution of the photosynthetic products by culturing the microalga under dark and anaerobic conditions; and
allowing a bacterium having a photosynthetic ability to act on the fermentation solution for hydrogen production under light and anaerobic conditions, wherein one or both of the process of culturing the microalga under light and aerobic conditions and the process of allowing the bacterium having a photosynthetic ability to act on the fermentation solution for hydrogen production under light and anaerobic conditions are performed with a transparent tower-type air-lift culture tank, the tower-type air-lift culture tank being a dual cylindrical structure in which a helical flow is generated;

wherein in the process of allowing the bacterium having a photosynthetic ability to act on the fermentation solution for hydrogen production under the light and anaerobic conditions, a lactic acid content is regulated to at least 0.3 mM.

2. A method for producing hydrogen comprising:

preparing photosynthetic products by culturing a microalga having a photosynthetic ability under light and aerobic conditions;

preparing a fermentation solution of the photosynthetic products by culturing the microalga under dark and anaerobic conditions; and allowing a bacterium having a photosynthetic ability to act on the fermentation solution for hydrogen production under light and anaerobic conditions, wherein a lactic acid content in the fermentation solution under the dark and anaerobic conditions is regulated to at least 0.3 mM.

3. The method of claim 1, wherein the following processes are performed continuously:

preparing photosynthetic products by culturing a microalga having a photosynthetic ability under light and anaerobic conditions;

preparing a fermentation solution of the photosynthetic products by culturing the microalga under dark and anaerobic conditions; and allowing a bacterium having a photosynthetic ability to act on the fermentation solution for hydrogen production under light and anaerobic conditions.

* * * * *

UNITED STATES PATENT AND TRADEMARK OFFICE
CERTIFICATE OF CORRECTION

PATENT NO.      : 6,395,521 B1
DATED           : May 28, 2002
INVENTOR(S)    : Yoshiharu Miura It is certified that error appears in the above-identified patent and that said Letters Patent is hereby corrected as shown below:

<u>Column 9,</u>
Line 14, "having *a" should read -- having a --.

Signed and Sealed this

Twenty-seventh Day of August, 2002

Attest:

Attesting Officer

JAMES E. ROGAN
*Director of the United States Patent and Trademark Office*